(12) United States Patent
Zhang et al.

(10) Patent No.: US 11,925,449 B2
(45) Date of Patent: Mar. 12, 2024

(54) ELECTRICAL IMPEDANCE IMAGING METHOD, SYSTEM, STORAGE MEDIUM, AND ELECTRONIC DEVICE

(71) Applicants: BEIJING HUARUI BOSHI MEDICAL IMAGING TECHNOLOGY CO., LTD., Beijing (CN); TSINGHUA UNIVERSITY, Beijing (CN)

(72) Inventors: Ke Zhang, Beijing (CN); Xin Zhang, Beijing (CN); Mingtao Guan, Beijing (CN); Yibing Wang, Beijing (CN)

(73) Assignees: BEIJING HUARUI BOSHI MEDICAL IMAGING TECHNOLOGY CO., LTD., Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 18/033,179

(22) PCT Filed: Aug. 18, 2021

(86) PCT No.: PCT/CN2021/113160
§ 371 (c)(1),
(2) Date: Apr. 21, 2023

(87) PCT Pub. No.: WO2022/083258
PCT Pub. Date: Apr. 28, 2022

(65) Prior Publication Data
US 2023/0329575 A1    Oct. 19, 2023

(30) Foreign Application Priority Data
Oct. 23, 2020    (CN) .......................... 202011145265.2

(51) Int. Cl.
*A61B 5/0536*    (2021.01)

(52) U.S. Cl.
CPC .................. *A61B 5/0536* (2013.01)

(58) Field of Classification Search
CPC .......... A61B 5/053–0537; A61B 5/063; A61B 5/0809; A61B 5/068; A61B 5/085;
(Continued)

(56) References Cited

U.S. PATENT DOCUMENTS

| | | | |
|---|---|---|---|
| 2003/0216664 A1 | 11/2003 | Suarez | |
| 2017/0105648 A1* | 4/2017 | Boverman | A61B 5/6843 |
| 2017/0172451 A1* | 6/2017 | Boverman | G06T 11/003 |

FOREIGN PATENT DOCUMENTS

| | | |
|---|---|---|
| CN | 109745046 A | 5/2019 |
| CN | 109781791 A | 5/2019 |

(Continued)

OTHER PUBLICATIONS

Machine Translation for JP-4755801-B2, Patent Translate, pp. 1-24, printed on Sep. 6, 2020 (Year: 2011).*

(Continued)

*Primary Examiner* — Yi-Shan Yang
*Assistant Examiner* — Om Patel
(74) *Attorney, Agent, or Firm* — Procopio, Cory, Hargreaves & Savitch LLP

(57) ABSTRACT

An electrical impedance imaging method, a system, a storage medium and an electronic device. Said method comprises: acquiring electrical impedance measurement signals of a tested human body area at a plurality of measurement times; for the electrical impedance measurement signal at each measurement time, constructing a corresponding instantaneous differential image on the basis of the electrical impedance measurement signal; constructing an image matrix on the basis of the instantaneous differential images corresponding to the plurality of measurement times, each column in the image matrix being a vector corresponding to (Continued)

the instantaneous differential image; determining, on the basis of the image matrix, a covariance matrix corresponding to the image matrix; obtaining, according to the covariance matrix, a weight vector of the covariance matrix; and obtaining, on the basis of the covariance matrix and the weight vector, an electrical impedance state image of the tested human body area.

11 Claims, 2 Drawing Sheets

(58) Field of Classification Search
CPC .............. A61B 5/14532; A61B 5/7264; A61B 2576/00–02; A61B 5/091
See application file for complete search history.

(56) References Cited

FOREIGN PATENT DOCUMENTS

| | | | | |
|---|---|---|---|---|
| CN | 109864712 | * | 6/2019 | |
| CN | 110251130 A | | 9/2019 | |
| CN | 110910466 A | | 3/2020 | |
| CN | 111067521 A | | 4/2020 | |
| CN | 111192337 A | | 5/2020 | |
| CN | 111281385 | * | 6/2020 | |
| CN | 111281385 A | | 6/2020 | |
| GB | 2559157 | * | 8/2018 | |
| JP | 4755801 B2 | * | 8/2011 | ........... A61B 5/0536 |
| WO | 2020/199367 A1 | | 10/2020 | |

OTHER PUBLICATIONS

Machine Translation for CN 111281385, Patent Translate, pp. 1-4, printed on Sep. 6, 2023, (Year: 2020).*

Machine Translation for CN 109864712, Patent Translate, pp. 1-13, printed on Sep. 6, 2023, (Year: 2019).*

International Preliminary Report on Patentability received in corresponding International Application No. PCT/CN2021/113160, dated Apr. 13, 2023, in 4 pages.

Written Opinion translation received in corresponding International Application No. PCT/CN2021/113160, dated Oct. 26, 2021, in 3 pages.

International Search Report (with translation) and Written Opinion received in corresponding International Application No. PCT/CN2021/113160, dated Oct. 26, 2021, in 11 pages.

Extended European Search Report received in corresponding EP App. No. 21881677.5, dated Jan. 17, 2024, in 9 pages.

* cited by examiner

ELECTRICAL IMPEDANCE IMAGING METHOD, SYSTEM, STORAGE MEDIUM, AND ELECTRONIC DEVICE

CROSS REFERENCE TO RELATED APPLICATIONS

This application is a 371 national stage application of International Patent Application No. PCT/CN2021/113160, filed, Aug. 18, 2021, which claims the priority of the Chinese patent application CN202011145265.2 entitled "Electrical Impedance Imaging Method, System, Storage Medium and Electronic Device", filed on Oct. 23, 2020, which is incorporated by reference in its entirety in this application.

FIELD OF THE INVENTION

The present disclosure pertains to the field of electrical impedance imaging technology, and in particular relates to a method, a system, a storage medium, and an electronic device for electrical impedance imaging.

BACKGROUND OF THE INVENTION

Current electrical impedance imaging techniques can only produce instantaneous electrical impedance change images, such as ones caused by instantaneous ventilation or blood perfusion. However, the instantaneous electrical impedance change images, such as blood perfusion images, change rapidly when displayed, which is detrimental to the understanding of the image by an observer. Moreover, the instantaneous electrical impedance change images often show relatively large differences in different human physiological cycles (e.g., the cardiac cycle), making it difficult for the observer to understand the overall functional state (e.g., ventilation or blood perfusion) of a tested human body area over a period of time.

SUMMARY OF THE INVENTION

The present disclosure presents a method, a system, a storage medium, and an electronic device for electrical impedance imaging, precisely based on the technical problem that it is difficult to reflect the overall state of a tested human body through instantaneous electrical impedance change images.

In a first aspect, the present disclosure provides an electrical impedance imaging method, comprising: acquiring electrical impedance measurement signals of a tested human body area at a plurality of measurement times; for the electrical impedance measurement signal at each measurement time, constructing a corresponding instantaneous differential image on the basis of the electrical impedance measurement signal; constructing an image matrix on the basis of the instantaneous differential images at the plurality of measurement times, wherein each column in the image matrix is a vector corresponding to respective instantaneous differential image; determining, on the basis of the image matrix, a covariance matrix corresponding to the image matrix; obtaining, according to the covariance matrix, a weight vector of the covariance matrix; and obtaining, on the basis of the covariance matrix and the weight vector, an electrical impedance state image of the tested human body area.

Optionally, the image matrix is:

$$I=(\alpha(t_1), \alpha(t_2), \ldots, \alpha(t_N))$$

where I is the image matrix, $\alpha(t_1)$ is a vector corresponding to the instantaneous differential image at a first measurement time, $\alpha(t_2)$ is a vector corresponding to the instantaneous differential image at a second measurement time, and $\alpha(t_N)$ is a vector corresponding to the instantaneous differential image at an N-th measurement time.

Optionally, the determining, on the basis of the image matrix, a covariance matrix corresponding to the image matrix, further comprises: calculating, on the basis of the image matrix, the covariance matrix corresponding to the image matrix by using a first predetermined computational equation, wherein, the first predetermined computational equation is:

$$C=(I-\bar{I})\cdot(I-\bar{I})^T$$

where C is the covariance matrix, I is the image matrix, T is a transpose of the matrix, $\bar{I}$ is a time-averaged matrix with the size of M*N, and each column element in the time-averaged matrix is $\bar{\alpha}=1/N\Sigma_{i=1}^{N}\alpha(t_i)$, where M is the number of pixels in each frame of instantaneous differential images, N is the number of measurement times, and $\alpha(t_i)$ is a vector corresponding to the instantaneous differential image at the i-th measurement time.

Optionally, the obtaining, according to the covariance matrix, a weight vector of the covariance matrix, further comprises: calculating the weight vector of the covariance matrix according to the covariance matrix by using a second predetermined computational equation, wherein the second predetermined computational equation is:

$$w_* = \arg\max_{w\in\{-1,1\}^M} w^T C w$$

where w* is the weight vector, w is a column vector with the size of M*1, the value of elements in the column vector is 1 or −1, T is a transpose of the matrix, and C is the covariance matrix.

Optionally, the obtaining, on the basis of the covariance matrix and the weight vector, an electrical impedance state image of the tested human body area, further comprises: calculating, on the basis of the covariance matrix and the weight vector, the electrical impedance state image of the tested human body area by using a third predetermined computational equation, wherein the third predetermined computational equation is:

$$a_s = C \cdot w^*$$

where $a_s$ is the electrical impedance state image, C is the covariance matrix, and w* is the weight vector.

Optionally, the for the electrical impedance measurement signal at each measurement time, constructing a corresponding instantaneous differential image on the basis of electrical impedance measurement signal, further comprises: for the electrical impedance measurement signal at each measurement time, extracting a signal in a predetermined frequency range from the electrical impedance measurement signal; and for each extracted signal in the predetermined frequency range, constructing a corresponding instantaneous differential image on the basis of the extracted signal in the predetermined frequency range by using an image reconstruction algorithm.

Optionally, the image reconstruction algorithm comprises a linear least square method.

In a second aspect, the present disclosure provides an electrical impedance imaging system comprising: an acquisition module, configured to acquire electrical impedance measurement signals of a tested human body area at a plurality of measurement times; an image construction module, configured to construct, for the electrical impedance measurement signal at each measurement time, a corresponding instantaneous differential image on the basis of the electrical impedance measurement signal; a matrix construction module, configured to construct an image matrix on the basis of the instantaneous differential images at the plurality of measurement times, wherein each column in the image matrix is a vector corresponding to respective instantaneous differential image; a covariance matrix calculation module, configured to determine, on the basis of the image matrix, a covariance matrix corresponding to the image matrix; a weight vector calculation module, configured to obtain, according to the covariance matrix, a weight vector of the covariance matrix; and a state image construction module, configured to obtain, on the basis of the covariance matrix and the weight vector, an electrical impedance state image of the tested human body area.

In a third aspect, the present disclosure provides a storage medium having program code stored thereon, wherein the electrical impedance imaging method as described in any of the above examples is implemented when the program code is executed by a processor.

In the fourth aspect, the present disclosure provides an electronic device, comprising a memory and a processor, wherein program code runnable on the processor is stored on the memory, and wherein the electrical impedance imaging method as described in any of the above examples is implemented when the program code is executed by the processor.

In the method, the system, the storage medium, and the electronic device for electrical impedance imaging provided in the present disclosure, an electrical impedance state image, which reflects the overall state of a tested human body function over a period of time, is reconstructed from the electrical impedance measurement signals of the tested human body area at a plurality of measurement times. As can be seen, the electrical impedance imaging method provided in the present disclosure can be used to obtain an electrical impedance state image that reflects the overall state of the tested human body function over a period of time, thereby facilitating the understanding of images and the overall grasp of the tested human body function by an observer for subsequent qualitative and quantitative analysis of the tested human body function.

BRIEF DESCRIPTION OF THE DRAWINGS

The scope of the present disclosure may be better understood by reading the detailed description of exemplary examples below in conjunction with the drawings. The drawings included herein are.

DETAILED DESCRIPTION OF THE INVENTION

In order to make the purpose, technical solutions and advantages of the present disclosure clearer, the implementation method of the present disclosure will be described in detail below in conjunction with the drawings and examples, whereby the implementation process of how technical means can be applied in the present disclosure to solve technical problems and achieve technical effects, can be fully understood and carried out accordingly.

While many specific details are set forth in the following description to facilitate a full understanding of the present disclosure, the present disclosure may also be implemented in other ways different from those described herein, and therefore the protection scope of the present disclosure is not limited by the specific examples disclosed below.

Example 1

Figure 1:
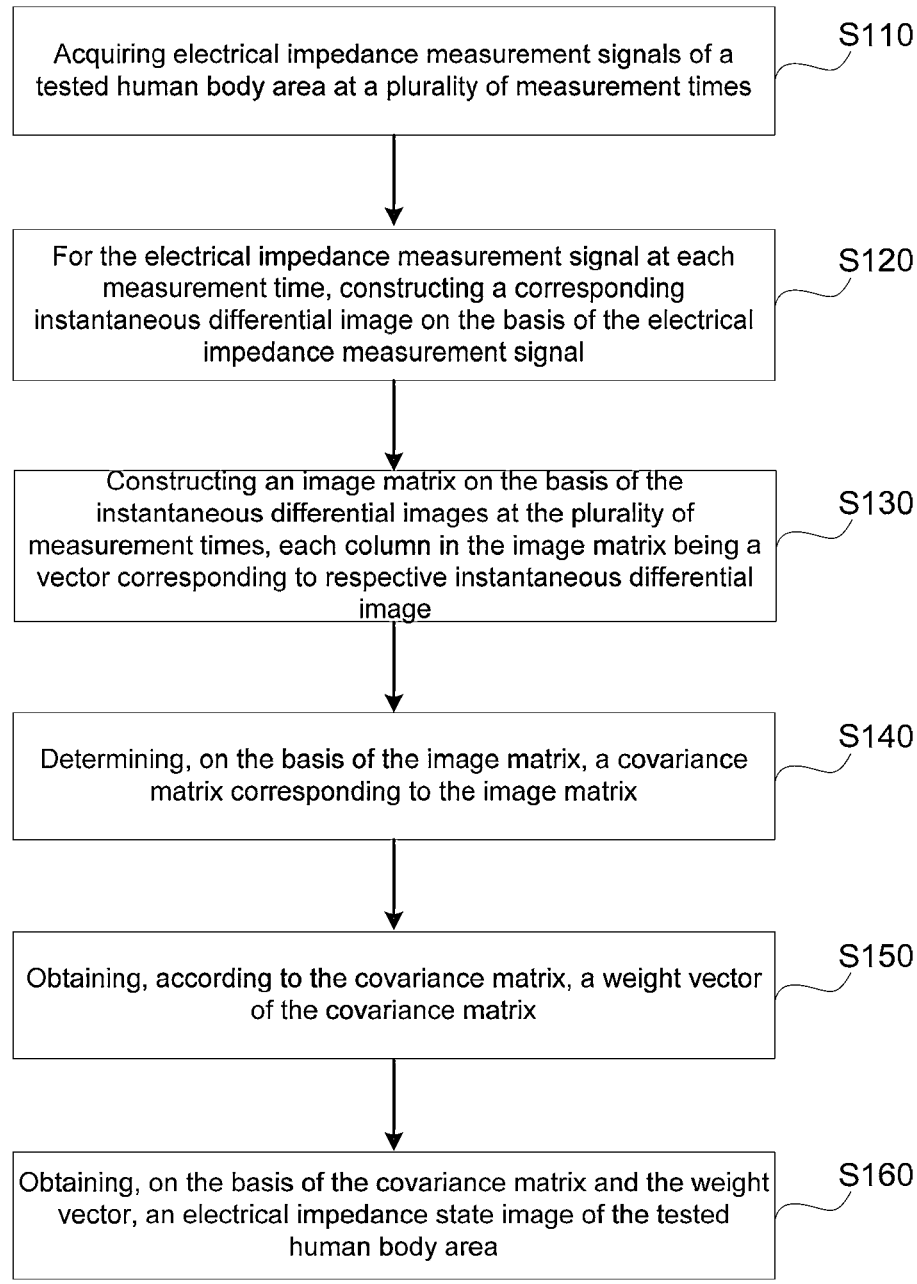
FIG. 1 illustrates a schematic flow diagram of an electrical impedance imaging method provided in Example 1 of the present disclosure.

According to examples of the present disclosure, an electrical impedance imaging method is provided, and FIG. 1 illustrates a schematic flow diagram of an electrical impedance imaging method provided in Example 1. As shown in FIG. 1, the electrical impedance imaging method may include steps S110 to S160 as follows.

In step S110, electrical impedance measurement signals of a tested human body area is acquired at a plurality of measurement times.

Here, the electrical impedance measurement requires first fixing an electrode array containing a number of electrodes around the tested human body area, and then exciting the tested human body area by the electrode array and measuring the resulting response. For example, the electrical impedance measurement signals are obtained by applying current excitation to the electrodes in turn and successively measuring the resulting voltage signals at other electrodes.

The plurality of measurement times means that the electrical impedance measurement is performed on the tested human body area several times over a continuous period of time, thereby obtaining the electrical impedance measurement signals at the plurality of measurement times.

In step S120, for the electrical impedance measurement signal at each measurement time, a corresponding instantaneous differential image is conducted on the basis of the electrical impedance measurement signal.

Here, after the electrical impedance measurement signal is obtained, the corresponding instantaneous differential image can be constructed on the basis of the electrical impedance measurement signal. If there are five measurement times, the instantaneous differential image corresponding to each of the five measurement times can be obtained.

The instantaneous differential image reflects the change in electrical impedance of the tested human body area at the measurement time of the reconstruction of the instantaneous differential image with respect to a reference time (e.g., the time corresponding to the end of expiration).

In an optional embodiment, in step S120, for the electrical impedance measurement signal at each measurement time, constructing a corresponding instantaneous differential image on the basis of the electrical impedance measurement signal, comprises steps S121 to S122 as follows.

Step S121, for each electrical impedance measurement signal at each measurement time, a signal in a predetermined frequency range is extracted from the electrical impedance measurement signal.

Step S122, for each extracted signal in the predetermined frequency range, a corresponding instantaneous differential image is constructed on the basis of the extracted signal in the predetermined frequency range by using an image reconstruction algorithm.

Here, in step S121, a signal in the predetermined frequency range is extracted from the electrical impedance measurement signals on the basis of the time-frequency characteristics of signals. The predetermined frequency range may be in a ventilation frequency range, then the extracted signal is a ventilation-related signal; and the predetermined frequency range may be in a blood perfusion frequency range, then the extracted signal is a blood perfusion-related signal. Specifically, a signal in the predetermined frequency range can be extracted from the electrical impedance measurement signals by using a filter.

After being extracted, the signal in the predetermined frequency range is used to construct a instantaneous differential image by an image reconstruction algorithm. The image reconstruction algorithm may be a differential reconstruction algorithm, such as a linear least square method.

It should be understood that although the linear least square method is used as the image reconstruction algorithm to reconstruct the instantaneous differential image in the present embodiment, those skilled in the art should understand that other image reconstruction algorithms may also be used in the present disclosure.

With the instantaneous differential image reconstruction of thoracic cavity blood perfusion taken as an example, the reconstruction process may be as follows: extracting a signal in a predetermined frequency range, i.e., a blood perfusion-related signal, from the electrical impedance measurement signals, and then performing the image reconstruction by using an image reconstruction algorithm on the basis of this blood perfusion-related signal to obtain a blood perfusion image.

In step S130, an image matrix is constructed on the basis of the instantaneous differential images at the plurality of measurement times. Each column in the image matrix is a vector corresponding to respective instantaneous differential image.

Here, after the instantaneous differential images corresponding to the plurality of measurement times are obtained, the image matrix is constructed by using the instantaneous differential images corresponding to the plurality of measurement times. This image matrix is:

$$I=(\alpha(t_1),\alpha(t_2), \ldots ,\alpha(t_N))$$

where I is the image matrix, $\alpha(t_1)$ is a vector corresponding to the instantaneous differential image at a first measurement time, $\alpha(t_2)$ is a vector corresponding to the instantaneous differential image at a second measurement time, and $\alpha(t_N)$ is a vector corresponding to the instantaneous differential image at an N-th measurement time.

In step S140, a covariance matrix corresponding to the image matrix is determined on the basis of the image matrix.

Here, a covariance matrix of this image matrix can be calculated after the image matrix is constructed.

In an optional embodiment, the determining of a covariance matrix corresponding to the image matrix on the basis of the image matrix further comprises the following process.

On the basis of the image matrix, the covariance matrix corresponding to the image matrix is calculated by using a first predetermined computational equation, wherein the first predetermined computational equation is:

$$C=(I-\bar{I})\cdot(I-\bar{I})^T$$

where C is the covariance matrix, I is the image matrix, T is a transpose of the matrix, $\bar{I}$ is a time-averaged matrix with a size of M*N, and each column element in the time-averaged matrix is $\bar{\alpha}=1/N\Sigma_{i=1}^{N}\alpha(t_i)$, where M is the number of pixels in each frame of instantaneous differential images, N is the number of measurement times, and $\alpha(t_i)$ is a vector corresponding to the instantaneous differential image at an i-th measurement time.

Here, each instantaneous differential image can be expressed as a column vector $\alpha(t_i)$, where $t_i$ is an i-th measurement time, i=1,2, . . . , N, and N is the number of measurement times. Each element in the vector $\alpha(t_i)$ represents a pixel value in the image. The image matrix is: $I=(\alpha(t_1), \alpha(t_2), \alpha(t_N))$, and the time-averaged matrix is a matrix with a size of M*N, and each column element in this matrix is $\bar{\alpha}$. Then a covariance matrix of the image matrix can be calculated by the first predetermined computational equation.

In step S150, according to the covariance matrix, a weight vector of the covariance matrix is obtained.

In an optional embodiment, the obtaining of a weight vector of the covariance matrix according to the covariance matrix further comprises the following process.

A weight vector of the covariance matrix is obtained according to the covariance matrix by using a second predetermined computational equation, wherein the second predetermined computational equation is:

$$w_* = \arg\max_{w\in\{-1,1\}^M} w^T C w$$

where w* is the weight vector, w is a column vector with the size of M*1, the value of elements in the column vector is 1 or −1, T is a transpose of the matrix, and C is the covariance matrix.

Here, the solution of the weight vector w* is actually to solve the 0-1 quadratic programming problem. Wherein, M is the total number of pixels in the image.

In step S160, on the basis of the covariance matrix and the weight vector, an electrical impedance state image of the tested human body area is obtained.

In an optional embodiment, the obtaining of an electrical impedance state image of the tested human body area on the basis of the covariance matrix and the weight vector further comprises the following process.

The electrical impedance state image of the tested human body area is obtained on the basis of the covariance matrix and the weight vector by using a third predetermined computational equation, wherein the third predetermined computational equation is:

$$a_s=C\cdot w^*$$

where $a_s$ is the electrical impedance state image, C is the covariance matrix, and w* is the weight vector.

Here, the electrical impedance state image can reflect the overall state of the tested human body area over a period of time, thus facilitating the understanding of the images and the overall grasp of the tested human body function by an observer, and thus facilitating subsequent qualitative and quantitative analysis of the tested human body function.

Figure 2:
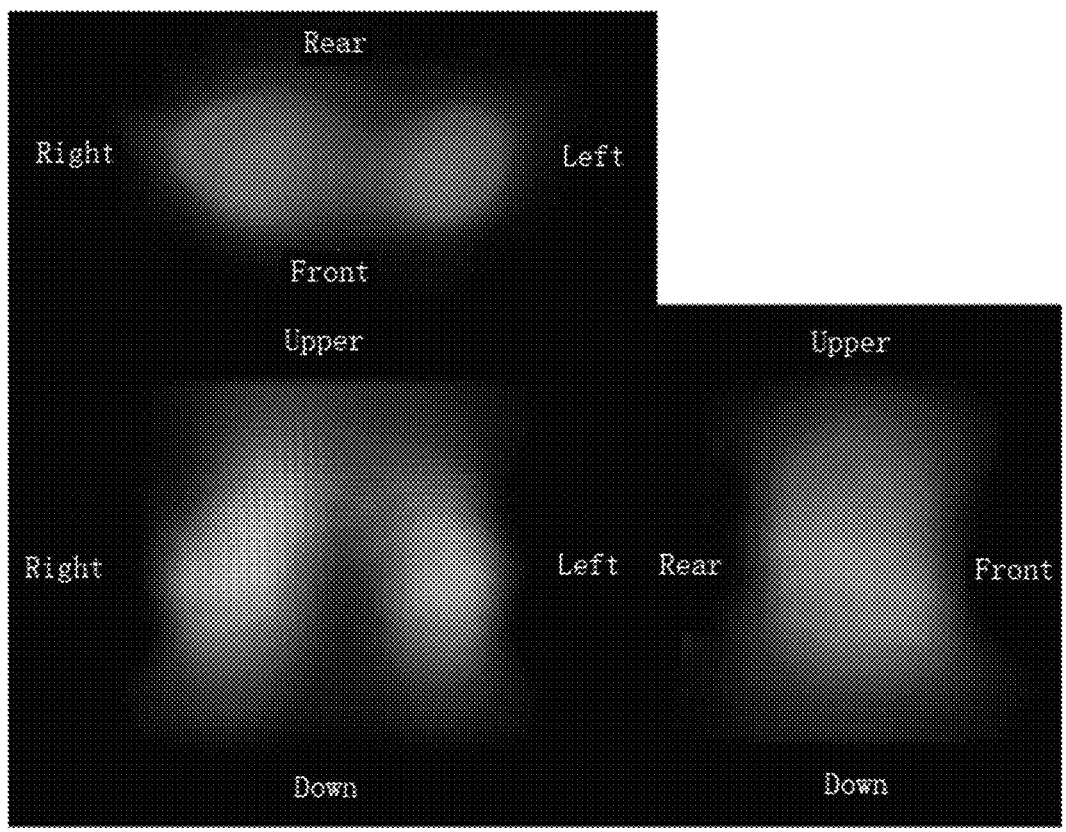
FIG. 2 illustrates an effect picture of an electrical impedance state image of three-dimensional blood perfusion in a human thoracic cavity.

FIG. 2 illustrates an effect picture of the electrical impedance state image of three-dimensional blood perfusion in a human thoracic cavity. As shown in FIG. 2, the electrical impedance state image reflects the electrical impedance state of three-dimensional blood perfusion in the human thoracic cavity for a period of time. Based on this image, it is easy for an observer to understand the image and grasp the overall situation of blood perfusion in the tested human body, which facilitates the subsequent qualitative and quantitative analysis of the tested human body function.

Example 2

According to examples of the present disclosure, an electrical impedance imaging system is also provided, which comprises an acquisition module, an image construction module, a matrix construction module, a covariance matrix calculation module, a weight vector calculation module, and a state image construction module.

The acquisition module is configured to acquire electrical impedance measurement signals of a tested human body area at a plurality of measurement times.

The image construction module is configured to construct, for the electrical impedance measurement signal at each measurement time, a corresponding instantaneous differential image on the basis of the electrical impedance measurement signal.

The matrix construction module is configured to construct an image matrix on the basis of the instantaneous differential images at the plurality of measurement times, wherein each column in the image matrix is a vector corresponding to respective instantaneous differential image.

The covariance matrix calculation module is configured to determine a covariance matrix corresponding to the image matrix on the basis of the image matrix.

The weight vector calculation module is configured to obtain a weight vector of this covariance matrix according to the covariance matrix.

The state image construction module is configured to obtain an electrical impedance state image of the tested human body area on the basis of the covariance matrix and the weight vector.

Example 3

According to examples of the present disclosure, a storage medium having program code stored thereon is also provided, wherein the electrical impedance imaging method as described in any of the above examples is implemented when the program code is executed by a processor.

Example 4

According to examples of the present disclosure, an electronic device comprising a memory and a processor is also provided, program code runnable on the processor is stored on the memory, and the electrical impedance imaging method as described in any of the above examples is implemented when the program code is executed by the processor.

The technical solutions of the present disclosure are described in detail above in conjunction with the drawings. Given that instantaneous electrical impedance change images in the related art can hardly reflect the overall state of the tested human body, the present disclosure provides an electrical impedance imaging method, a system, a storage medium, and an electronic device, an electrical impedance state image reflecting the overall state of the tested human body function over a period of time is reconstructed from electrical impedance measurement signals of the tested human body area at a plurality of measurement times. As can be seen, an electrical impedance state image reflecting the overall state of the tested human body function over a period of time can be obtained by using the electrical impedance imaging method provided by the examples of the present disclosure, thereby facilitating the understanding of the images and the overall grasp of the tested human body function by an observer for subsequent qualitative and quantitative analysis of the tested human body function.

In the several examples provided in the present application, it should be understood that the disclosed device and method can be implemented in other ways. For example, the device examples described above are merely schematic, e.g., the division of units, which is only a logical functional division, can be performed in other ways in actual implementation. For example, a plurality of units or assemblies can be combined or integrated into another system, or some features can be ignored, or not implemented.

The units illustrated as isolated components may or may not be physically separated, and the components displayed as units may or may not be physical units, i.e. they may be located in one position or may be distributed to a plurality of network units. Some or all of these units may be selected based on practical needs to achieve the purpose of examples in the present disclosure.

In addition, each functional unit in each example of the present disclosure may be integrated in a single processing unit, or each functional unit may be present in physical separation, or two or more units may be integrated in a single processing unit. The above integrated units can be implemented in the form of either hardware or software functional units.

The integrated unit, when implemented in the form of software functional units and sold or used as a separate product, may be stored in a computer readable storage medium. Based on this understanding, the essence of the technical solution of the present disclosure, or in other words, a part thereof contributing to the prior art, or all or parts of the technical solution may be embodied in the form of a software product. The software product is stored in a storage medium and includes a number of instructions to enable an electronic device (which may be a personal computer, a server, or a network device, etc.) to perform all or some of the steps in various examples of the present disclosure. The aforementioned storage medium includes: USB flash drives, portable hard drives, Read-Only Memories (ROM), Random Access Memories (RAM), disks, or compact discs, and various other media that can store a program code.

Although the present disclosure discloses embodiments as described above, the described contents are only embodiments adopted to facilitate the understanding of the present disclosure and are not intended to limit the present disclosure. Those skilled in the art to which the present disclosure pertains may make any modifications and changes in the form and details of implementation without departing from the spirit and scope of the present disclosure. However, the protection scope of the present disclosure shall be still defined in the appended claims.

The invention claimed is:

1. An electrical impedance imaging method, comprising:
   acquiring electrical impedance measurement signals of a tested human body area at a plurality of measurement times;
   for the electrical impedance measurement signal at each measurement time, constructing a corresponding instantaneous differential image on a basis of the electrical impedance measurement signal;
   constructing an image matrix on a basis of the instantaneous differential images at the plurality of measurement times, wherein each column in the image matrix is a vector corresponding to the respective instantaneous differential image, and wherein the image matrix is:

$$I=(\alpha(t_1),\alpha(t_2),\ldots,\alpha(t_N))$$

where I is the image matrix, $a(t_1)$ is a vector corresponding to the instantaneous differential image at a first measurement time, $a(t_2)$ is a vector corresponding to the instantaneous differential image at a second measurement time, and $a(t_N)$ is a vector corresponding to the instantaneous differential image at an N-th measurement time;

determining, on a basis of the image matrix, a covariance matrix corresponding to the image matrix;

obtaining, according to the covariance matrix, a weight vector of the covariance matrix; and obtaining, on a basis of the covariance matrix and the weight vector, an electrical impedance state image of the tested human body area.

2. The method according to claim 1, wherein the acquiring electrical impedance measurement signals of the tested human body area at the plurality of measurement times further comprises:

fixing an electrode array around the tested human body area, wherein the electrode array comprises a plurality of electrodes; and exciting the tested human body area by the electrode array and measuring a resulting response.

3. The method according to claim 1, wherein the determining, on the basis of the image matrix, the covariance matrix corresponding to the image matrix, further comprises:

calculating, on the basis of the image matrix, the covariance matrix corresponding to the image matrix by using a first predetermined computational equation, wherein the first predetermined computational equation is:

$$C = (I - \bar{I}) \cdot (I - \bar{I})^T$$

where C is the covariance matrix, I is the image matrix, T is a transpose of the matrix, $\bar{I}$ is a time-averaged matrix with a size of M*N, and each column in the time-averaged matrix is $\bar{a} = 1/N \sum_{i=1}^{N} a(t_i)$, where M is a number of pixels in each frame of the instantaneous differential images, N is a number of measurement times, and $a(t_i)$ is a vector corresponding to the instantaneous differential image at an i-th measurement time.

4. The method according to claim 1, wherein the obtaining, according to the covariance matrix, the weight vector of the covariance matrix, further comprises:

calculating, according to the covariance matrix, the weight vector of the covariance matrix by using a second predetermined computational equation, wherein the second predetermined computational equation is:

$$w_* = \arg\max_{w \in \{-1,1\}^M} w^T C w$$

where w* is the weight vector, w is a column vector with a size of M*1, a value of elements in the column vector is 1 or −1, T is a transpose of the matrix, and C is the covariance matrix.

5. The method according to claim 1, wherein the obtaining, on the basis of the covariance matrix and the weight vector, the electrical impedance state image of the tested human body area, further comprises:

calculating, on the basis of the covariance matrix and the weight vector, the electrical impedance state image of the tested human body area by using a third predetermined computational equation, wherein the third predetermined computational equation is:

$$a_s = C \cdot w^*$$

where $a_s$ is the electrical impedance state image, C is the covariance matrix and w* is the weight vector.

6. The method according to claim 1, wherein the constructing, for the electrical impedance measurement signal at each measurement time, the corresponding instantaneous differential image on the basis of the electrical impedance measurement signal, further comprises:

for the electrical impedance measurement signal at each measurement time, extracting a signal in a predetermined frequency range from the electrical impedance measurement signal; and for each extracted signal in the predetermined frequency range, constructing the corresponding instantaneous differential image on the basis of the extracted signal in the predetermined frequency range by using an image reconstruction algorithm.

7. The method according to claim 6, wherein the signal in the predetermined frequency range is extracted from the electrical impedance measurement signals by using a filter.

8. The method according to claim 6, wherein the extracted signal is a ventilation-related signal or a blood perfusion-related signal.

9. The method according to claim 6, wherein the image reconstruction algorithm comprises a linear least square method.

10. A non-transitory storage medium having a program code stored thereon, wherein the electrical impedance imaging method according to claim 1 is implemented when the program code is executed by a processor.

11. An electronic device, comprising a memory and a processor, wherein program code runnable on the processor is stored on the memory, and wherein the electrical impedance imaging method according to claim 1 is implemented when the program code is executed by the processor.

* * * * *